US00PP34612P2

(12) United States Plant Patent
Swartz

(10) Patent No.: US PP34,612 P2
(45) Date of Patent: Sep. 27, 2022

(54) STRAWBERRY PLANT NAMED 'QBC-1'

(50) Latin Name: ***Fragaria* spp.**
Varietal Denomination: Strawberry plant named 'QBC-1'

(71) Applicant: Five Aces Breeding LLC, Naples, NY (US)

(72) Inventor: Harry Jan Swartz, Naples, NY (US)

(73) Assignee: Five Aces Breeding LLC, Naples, NY (US)

( * ) Notice: Subject to any disclaimer, the term of this patent is extended or adjusted under 35 U.S.C. 154(b) by 0 days.

(21) Appl. No.: 17/803,153

(22) Filed: Mar. 8, 2022

(51) Int. Cl.
*A01H 6/74* (2018.01)
*A01H 5/08* (2018.01)

(52) U.S. Cl.
USPC ..... Plt./209

(58) Field of Classification Search
USPC ..... Plt./209
See application file for complete search history.

*Primary Examiner* — Annette H Para
(74) *Attorney, Agent, or Firm* — Hueschen and Sage

(57) ABSTRACT

A new and distinct variety of strawberry plant 'QBC-1' specifically suited to the retail trade. It is reminiscent of wild strawberry, producing very sweet fruit with strong strawberry aroma and wild fruit size and plant vigor. Compared to soft fleshed wild strawberries, the new variety 'QBC-1' is more productive and has fruit flesh which is melting and can be stored for longer periods. The fruit has a light pink color offset with darker red achenes (seeds).

9 Drawing Sheets

Latin name:
Botanical classification: *Fragaria* spp.
Variety denomination: Strawberry plant named 'QBC-1'.

BACKGROUND OF THE INVENTION

The present invention relates to a strawberry genotype selected to provide a cultivar with attributes of wild fruit for smaller scale growers, the general public or niche marketing commercial growers who provide for high end markets. Compared with other wild type strawberries offered in retail outlets, the present invention is of similar size, less likely to show fruit damage than white fruited varieties, more productive, has a reasonable shelf and freezer life, high sugar content and a pleasant and strong strawberry aroma. Its flowering season is late, reducing the possibility of frost damage, and harvest is over a four-week period as compared to a shorter period on other spring bearing wild species.

BRIEF SUMMARY OF THE INVENTION

This invention concerns a new and distinct cultivar of short day fruiting strawberry plant designated: 'QBC-1', with a botanical name of *Fragaria* spp. 'QBC-1' provides one or more advantages compared to the parental and/or other strawberry varieties.

Strawberry plant variety 'QBC-1' was discovered in a strawberry breeding test plot in Moseley, Va. and originated from a cross between the female parent 'NAR-v1' (unpatented) and the male parent 'White Carolina' (unpatented). A single plant was selected and asexually propagated via stolon plants in Oakland, Md. and subsequently in South Bristol, N.Y., Watsonville, Calif. and Lacota, Mich.

The plants so propagated have shown that the unique features of this new *Fragaria* variety 'QBC-1' are stable and reproduce true to type through successive generations of asexual reproduction via stolon plants and micropropagation in branch crown based tissue culture.

Strawberry plant variety 'QBC-1' originated from a cross of 'NAR-v1' (female parent; unpatented) x 'White Carolina' (male parent; unpatented, US Department of Agriculture National Clonal Germplasm Repository PI number 551681), an heirloom variety of white fruited strawberry. 'NAR-v1' (unpatented) was selected in a strawberry breeding plot at a farm in Virginia on Apr. 29, 2018. It was small fruited, light colored fleshed, red skinned selection which was moderately productive.

'NAR-v1' was derived from a cross of 'FEC-v1' x 'IFA-c1'. 'FEC-v1' (unpatented) contains only *Fragaria* x *ananassa* germplasm. 'IFA-c1' (unpatented) was a cross of 'GDT-v8' (unpatented) x '02ak187', an unpatented selection from a breeding plot in the United Kingdom. 'GDT-v8' was a third generation backcross with 'SO8183' (unpatented), a synthetic octoploid containing *Fragaria vesca* L., *Fragaria moschata* Duch. and *Fragaria nubicola* (Hook.f) Lindl. (Bors and Sullivan, 2005).

Strawberry plant variety 'QBC-1' is distinguished from other cultivars by its origin, its mature fruit coloration, productivity, flavor, high sugar level, ease of removal of the calyx from the fruit, melting flesh and small fruit size.

'QBC-1' is not suitable for premium commercial harvest and shipping due to its softness and fruit size. 'QBC-1' is intended for use as a replacement to white fruited wild or heirloom varieties used for the retail trade, primarily due to its productivity relative to other wild genotypes, and flavor.

BRIEF DESCRIPTION OF THE DRAWINGS

The accompanying photographs illustrate the overall appearance of the new and distinct variety of 'QBC-1'.

DETAILED BOTANICAL DESCRIPTION

Figure 1:
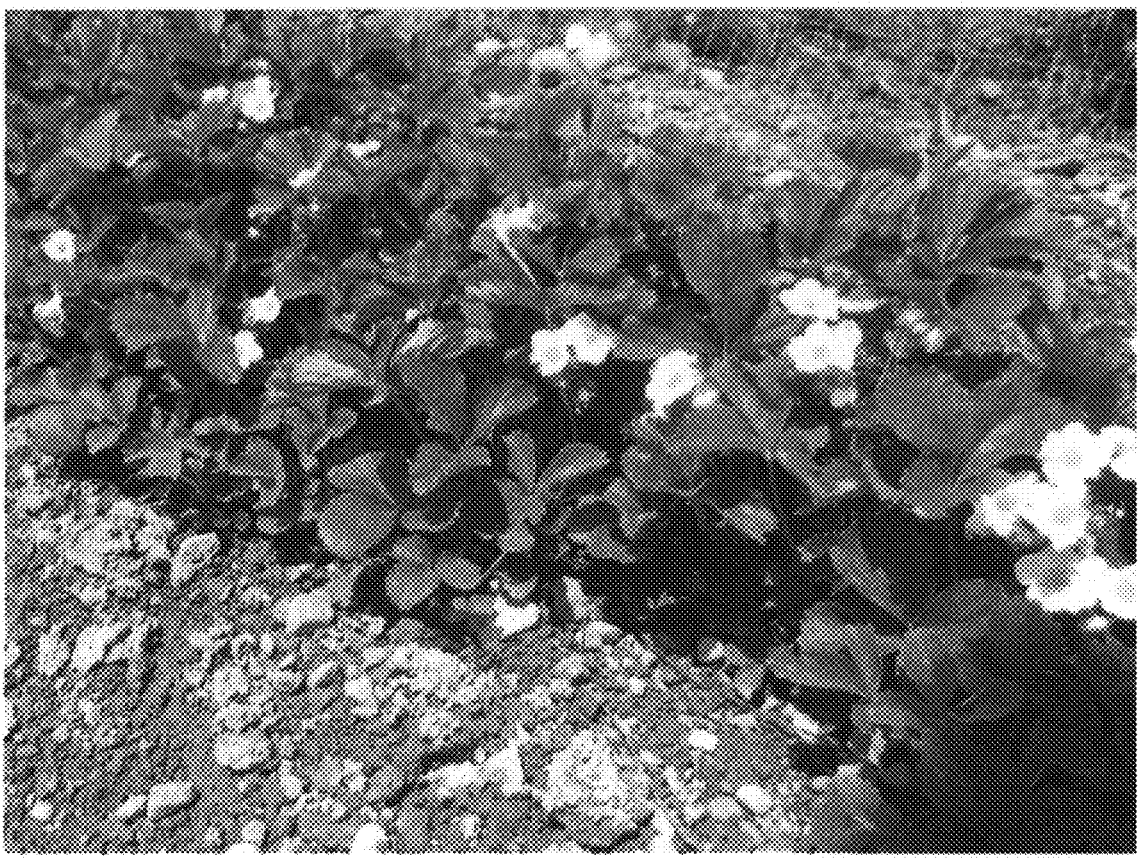
FIG. 1. A section of 'QBC-1' plants grown in central New York, USA in a runner produced matted row one year after planting showing leaf and flower truss characteristics.

The following is a detailed botanical description of the new and distinct variety of strawberry plant 'QBC-1', its flower, fruit, foliage and trusses, based on observation of specimens.

Statements of characteristics herein represent exemplary observations of the cultivar herein. Where dimensions, sizes, colors, and other characteristics are given, it is to be understood that such characteristics are approximations and averages. The field observations reported herein are largely based on observations made on mature plants located in plots in central Virginia, USA and central New York, USA. The specimens were propagated from the original plant and have retained the characteristics of the original selection.

Cultivar name—'QBC-1'.

Family—Rosaceae.

Botanical name—*Fragaria* spp.

Common name—Strawberry.

Parentage: Female parent—'NAR-v1' (unpatented). Male parent—'White Carolina' (unpatented).

Color descriptions, except those given in common terms, use designations cited from The Royal Horticultural Society (R.H.S.) Colour Chart. Original publication date 1966, second publication date 1995. Colors in the drawings are only approximate, in cases where the colors in the drawings differ from the R.H.S. color designation given herein, the RHS designation should be considered accurate.

The following measurements were from a mature plant and yielding fruits.

Vegetative Habit. 'QBC-1' plants are stoloniferous perennials, very vigorous and runner freely, producing an average of 64 runner plants per mother plant. 'QBC-1' stolons are usual for the genus, with a single sheathed proximal bud that is usually dormant and an apical meristem that develops into a crown which eventually roots to form a new plant. 'QBC-1' produces runners earlier than most cultivated strawberry varieties, as early as flowering on plants with a full crop. A matted row of runner plants is readily formed during the year of planting (FIG. 1).

Figure 2:
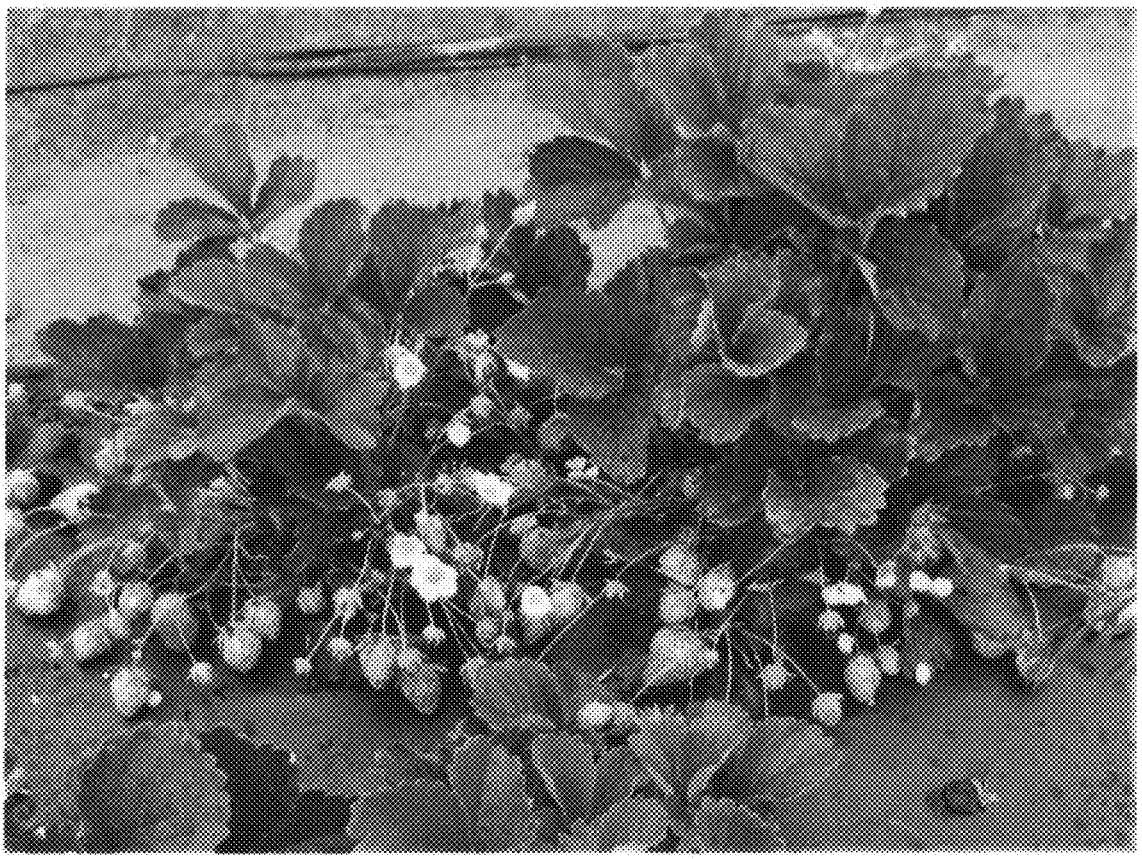
FIG. 2. Two 'QBC-1' plants as grown in a fall planted, no runner, plasticulture system in central Virginia showing leaf and fruiting characteristics. Lower branched trusses and prolonged flowering occur because plants are cold protected during their flower initiation period.

When runners are removed after planting, on average 12 crowns and 89.5 leaves are produced per plant when counted the subsequent year during flowering. Internal crown color is yellow, reminiscent of RHS plate 11C. Runner removed plants are spreading and relatively short to moderate height and have an average diameter of 62 cm and a height of 35 cm on average (FIG. 2). Newly formed leaves are erect, but eventually become prostrate after months of growth. Leaves are pinnately trifoliolate as is typical of the genera, with the terminal leaflet on average 9.7 cm in length along the midrib and 9.5 cm at the maximum blade width. Leaf shape is obovate with margins serrulate, non-reflexed, or continuous with the rest of the leaf blade and number 18 per typical leaflet. The terminal leaflet is obovate with a round distal terminus and an attenuated leaf base with a simple, entire, margin. Leaf veins are arranged in an arcuate fashion and protrude over half their diameter above the abaxial lamina surface. The leaf in cross section is broadly rolled inward or concave and not strongly rugose. The terminal leaflet is attached to a petiolule of 0.4 to 2.1 cm in length.

At the maximum width, the two lateral leaflets have a similar shape compared to the terminal leaflet, with an average 10.5 cm in length. Lateral leaflets are eccentric, with 3.9 cm width above (distal) their midrib and 5.4 cm proximal or below the midrib. The lateral leaflets are opposite and attached to the petiole with a petiolule which averages 1.3 cm in length.

Leaf color is greyed green and depending on fertilization, can be RHS Plate 189A or 189B on the top, adaxial side, and 191B on the bottom, abaxial side. The adaxial leaf lamina is strongly glabrous, while the abaxial lamina is moderately tomentose.

Figure 3:
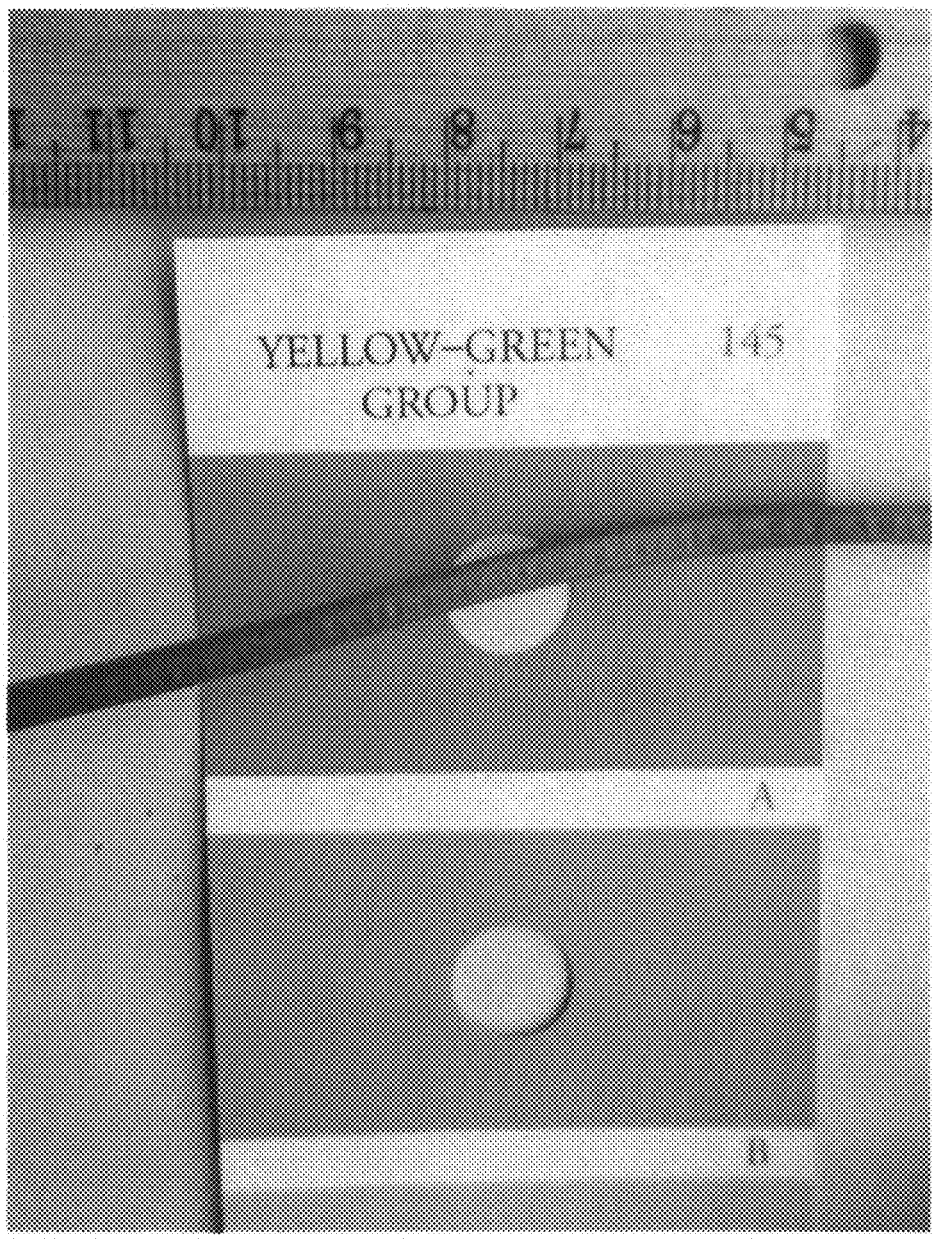
FIG. 3. A 'QBC-1' petiole showing RHS plate 145.

Petioles are moderately hirsute with soft hair of varying lengths arranged perpendicular to the axis of the petioles, trusses and petiolule. Petioles average 30.6 cm in length, with a diameter of 0.4 cm at their half way point. The leaf petiole color is yellow-green and reminiscent of RHS plate 145A (FIG. 3). Petioles have two narrowly acute stipules averaging 2.1 cm in length and 0.4 cm width at their base.

Figure 4:
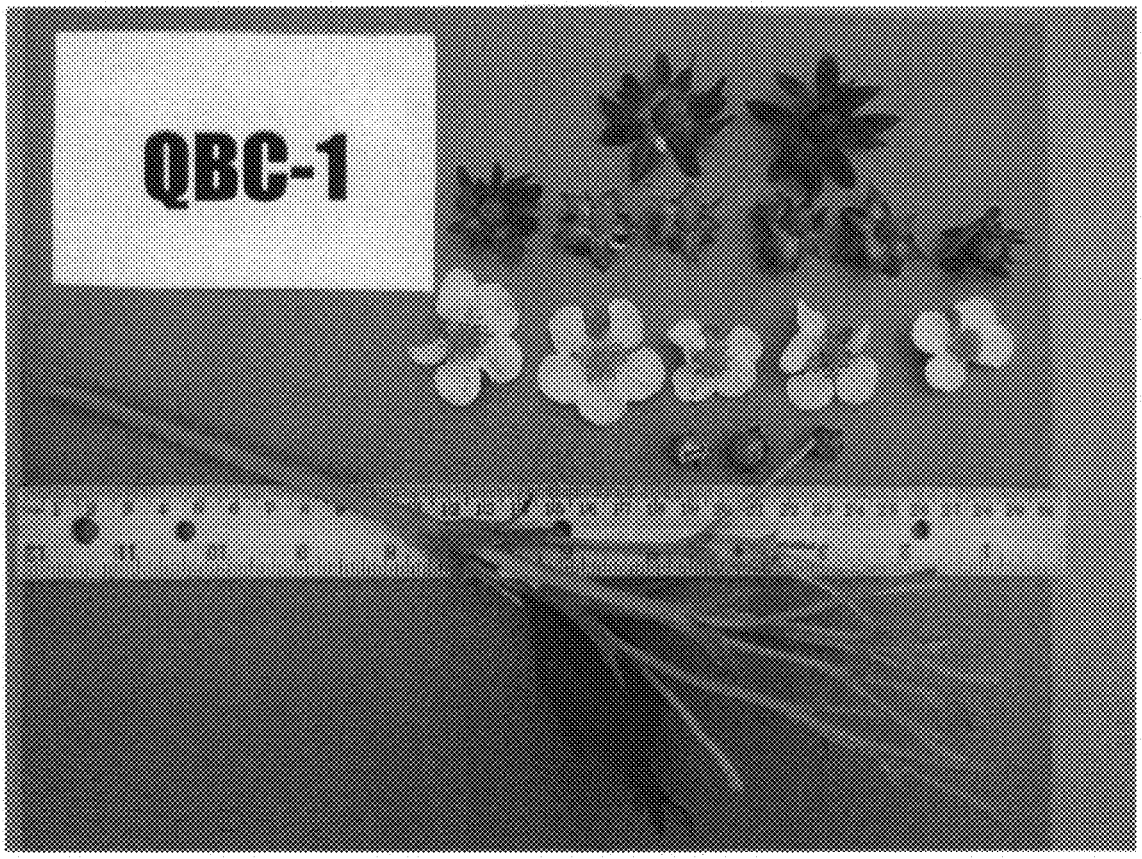
FIG. 4. A mid branched 'QBC-1' flower truss with the flowers removed and arranged by flowering sequence. The truss was removed at the crown on the left side of the illustration.

Floral habit. On runner removed plants, on average, 5.3 trusses will be formed from the crown. Runner daughter plants have one or two trusses, depending on the length of time the runner plants formed and rooted the previous growing season. Independent of cultural treatment, trusses are racemes with the cymose habit of initial or proximal branching tending to arise from a single branch point, 'QBC-1' trusses have earlier flowering primary flowers and successively smaller, later flowering, secondary, tertiary and higher order flowers on truss branches (FIG. 4). On runner removed plants, the truss can produce on average a single primary flower, 3.3 secondary flowers and 7.3 tertiary flowers. On runner plants with one truss, the largest trusses produce, on average, 2 primary, 6 secondary, 5 tertiary, 3 quarternary and 5 quinary flowers.

Figure 5:
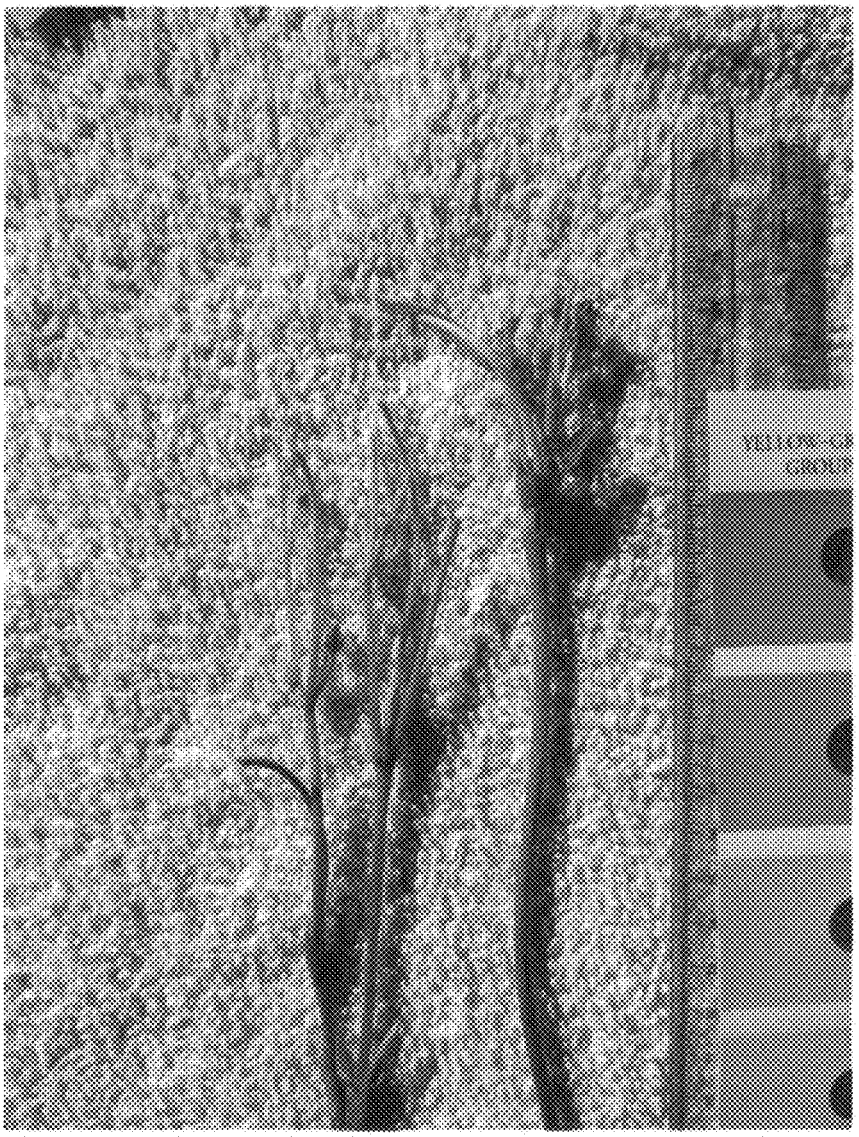
FIG. 5. A low branched (bottom) and a high branched (top) truss with flowers removed from two different 'QBC-1' plants with a millimeter (mm) gradation ruler and RHS plate 145.

Branching structure varies with low branched trusses: 1 cm to the first branch point from their attachment to the crown, then 5, 6, 3 and 2 cm to the second, third, fourth and terminal branch points (FIG. 5). On other trusses, the truss branches more distal to the crown with the first branch 6.8 to 15.5 cm (average 7.8 cm) distal to the crown and secondary branches 4.4 to 6.7 cm distal to the first branch point. Lower branched trusses are more typical of colder weather floral initiation, such as occurs in row cover protected Virginia grown plants (vs. New York grown) and less frequent in 'QBC-1' than genotypes used for commercial production. Highly dissected, higher branched trusses are more typical of the *Fragaria* wild species used as parents.

Low to middle branched trusses typically contain an ascending lanceolate monofoliolate leaf which is often reduced to a bract on distal branched trusses (FIG. 4). The largest monofoliolate leaves are 2 to 8 cm in length along the midrib and 0.5 to 5 cm wide at their maximum width. Monofoliolate leaves are attached to the truss with 0.2 to 3 cm petioles. Bracts also occur at branch points and average 1 cm in length and 0.3 to 0.95 cm in width at their base, which is wrapped around the truss. Monofoliolate leaves have the same color as vegetative leaves and trusses have the same color as petioles. The truss, which bear the fruit, are peduncles and are reminiscent of RHS plate 145A through 145B. Trusses raise the flowers to or very slightly above the leaf canopy.

Figure 6:
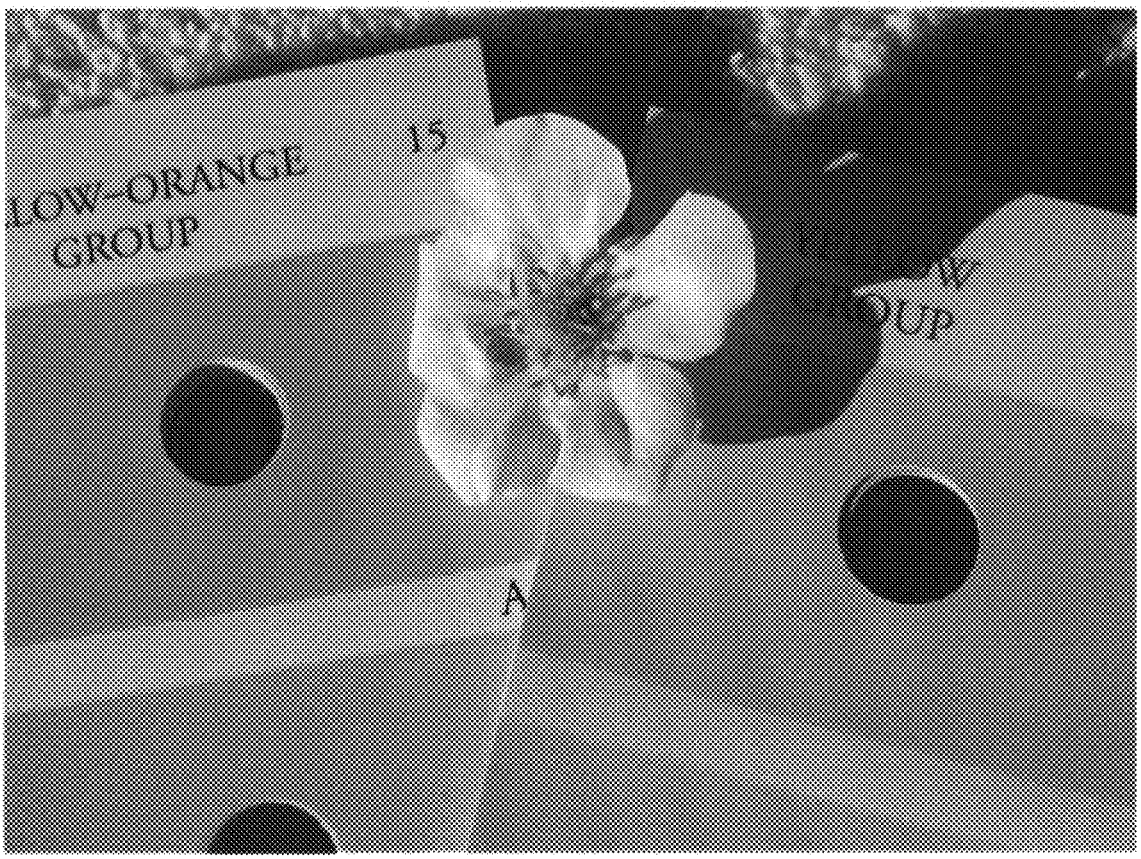
FIG. 6. A mid-season flower from 'QBC-1' and RHS plates 15 (left) and 10.
Figure 7:
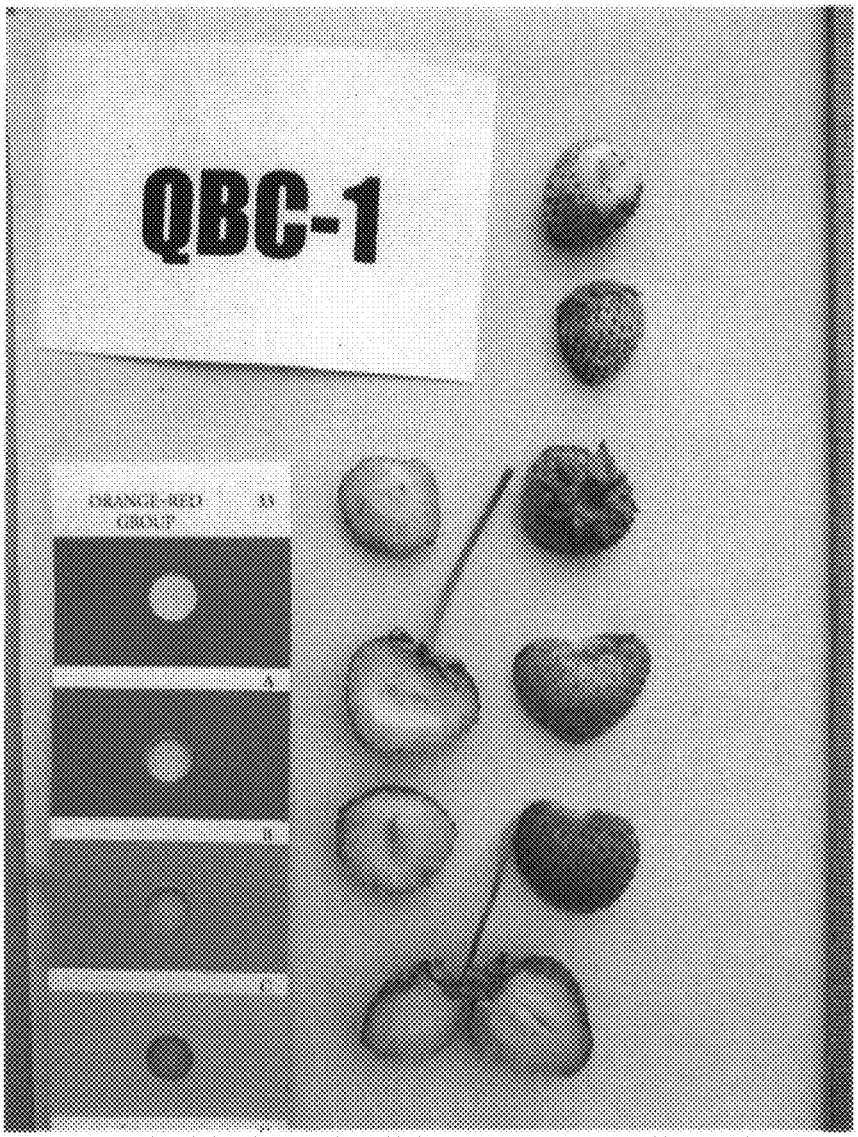
FIG. 7. A ripening series of 'QBC-1' fruit and RHS plate 33 and a mm gradation ruler on the right margin.

Flowers. 'QBC-1' flowers are perfect and self-fertile (FIG. 6). Under normal conditions and without hives, less than 5% of the pistils fail to develop into achenes with seed. Sepals and petals are arranged radially, around a ring of, on average 40.5 stamen and center receptacle with an average of 175.2 pistils in larger primary flowers. Stamen height averages 0.3 cm. Anthers are yellow, reminiscent of RHS plate 15 A and 15B (FIG. 6), with their center turning RHS 3A upon dehiscence. At flowering, the pistil color, overall, is yellow, reminiscent of RHS plate 10A. Receptacle diameter at flowering is 0.4 cm, growing to 0.7 cm at petal fall. Petals average five in number and are white, RHS plate 155C. Petals are orbicular with entire margins and slightly rugose. Sepals at flowering are lanceolate and fused broadly with a slight depression to the calyx at their base which develops later in ripening (FIG. 7). Number of sepals varies with fruit size and cultural system but range from 6.7 on tertiary flowers to 22.0 on primary flowers. Sepal length averages 1.3 cm and width at the base averages 0.3 cm. Sepal color on the adaxial surface was greyed green reminiscent of RHS plate 190A along the edges. Sepals are arranged around the petals in an overlapping fashion and greyed-green, RHS plate 193B, in the center. The abaxial sepal surface was also greyed green reminiscent of RHS plate 194A. Upon fruit ripening sepals can lose some of their green pigment and color can change to RHS plate 145A. Typical flowering occurs in mid-May in the Finger Lakes region of New York and mid-April in central Virginia.

Figure 8:
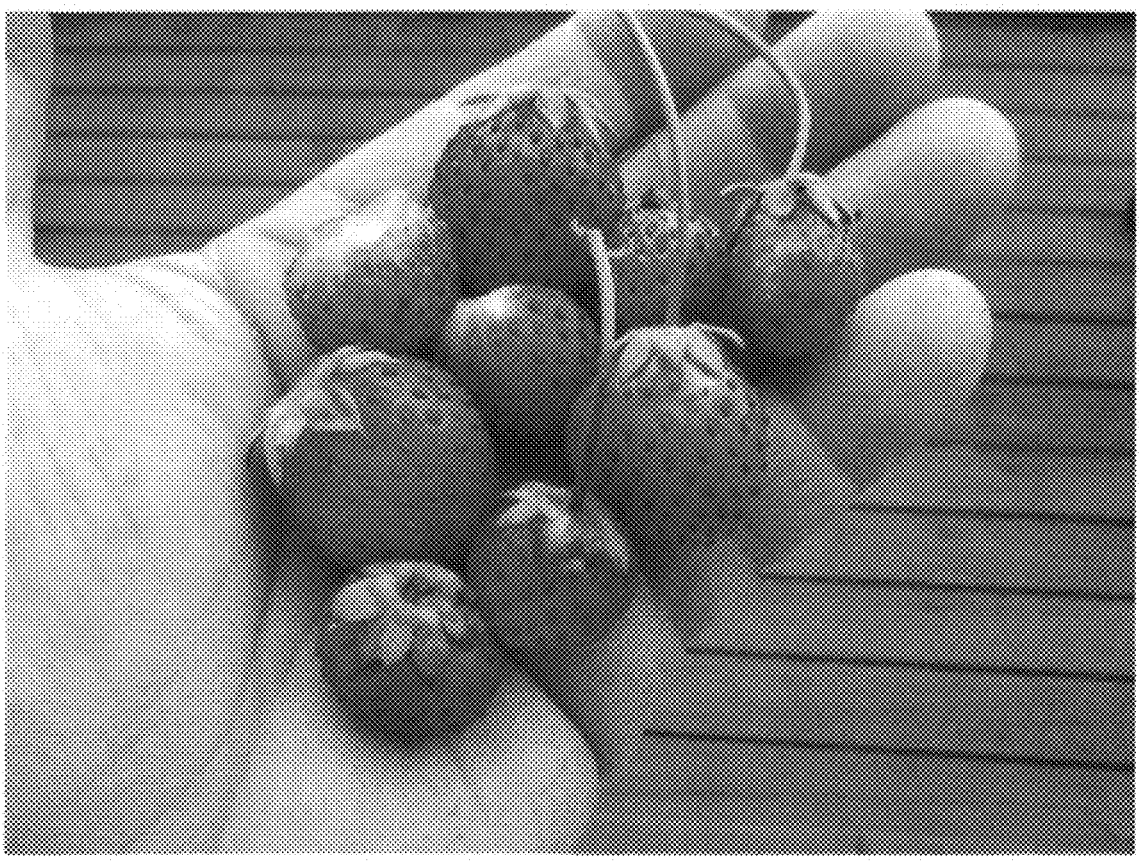
FIG. 8. A group of 'QBC-1' fruit showing seed coloration, attachment and arrangement and loss of sepals during harvest.

Fruit. After petal fall, the receptacle is green-yellow colored mostly by expanding seeds and is reminiscent of RHS plate 145A to 145C (FIG. 4). Unripe fruit develops yellow color RHS plate 1D internally. Early ripening and fruit softening occurs about 4 weeks after flowering and any red color is reminiscent of RHS plate 26D. Ripe fruit are orange-red and reminiscent of RHS color plate 33A in the darkest, well lighted parts of the fruit to 33C in the shady side of the fruit (FIG. 7). The internal flesh of the fruit has some red pigment on the nearest the skin, reminiscent of RHS plate 36C with white internal flesh reminiscent of RHS plate 155D. There is no streaking of color along vascular traces, with color gradually disappearing from outside the fruit to its center. Some slight fractures or spaces occur internal to ripe fruit, typically about a 1 cm long and less than 0.1 cm across as seen on a cut surface. Seed (achene) color is red, reminiscent of RHS plate 46A in sun lighted areas of the fruit and yellow green, RHS plate 145A or 145B in shaded sections of the fruit. Seeds are well attached to the receptacle and ovoid with a broadly acute stigma and style end, which are remnants on the seed before ripening. Seeds sit moderately deep, half buried, in slight depressions in the receptacle surface (FIG. 8).

Harvest Data. In a 35 ft (10.7 m) matted row planted in 2020, the following yields were obtained: June 11, 2044 grams; June 16, 2333 grams; June 20, 2014 grams; June 28, 1521 grams; July 3, 89 grams. Total yield was 8001 grams; which is equal to 750.6 g per meter or 0.489 pounds per foot of row. Fruit weights on the same dates averaged 5.54 g; 4.67 g; 4.38 g; 3.85 g; and 2.28 grams. Soluble solids, as determined by refractometer in 2021, were 7.0 on June 16; 9.3 on June 20; 11.0 on June 28 and 9.9 on 6 month-old frozen fruit. Sepals remained on the plant on 69.6% of the fruit picked on June 11. On June 28, only 4% of the caps remained on the plant. First harvest fruit on plants given no fungicidal treatment were 98% clean and marketable.

Figure 9:
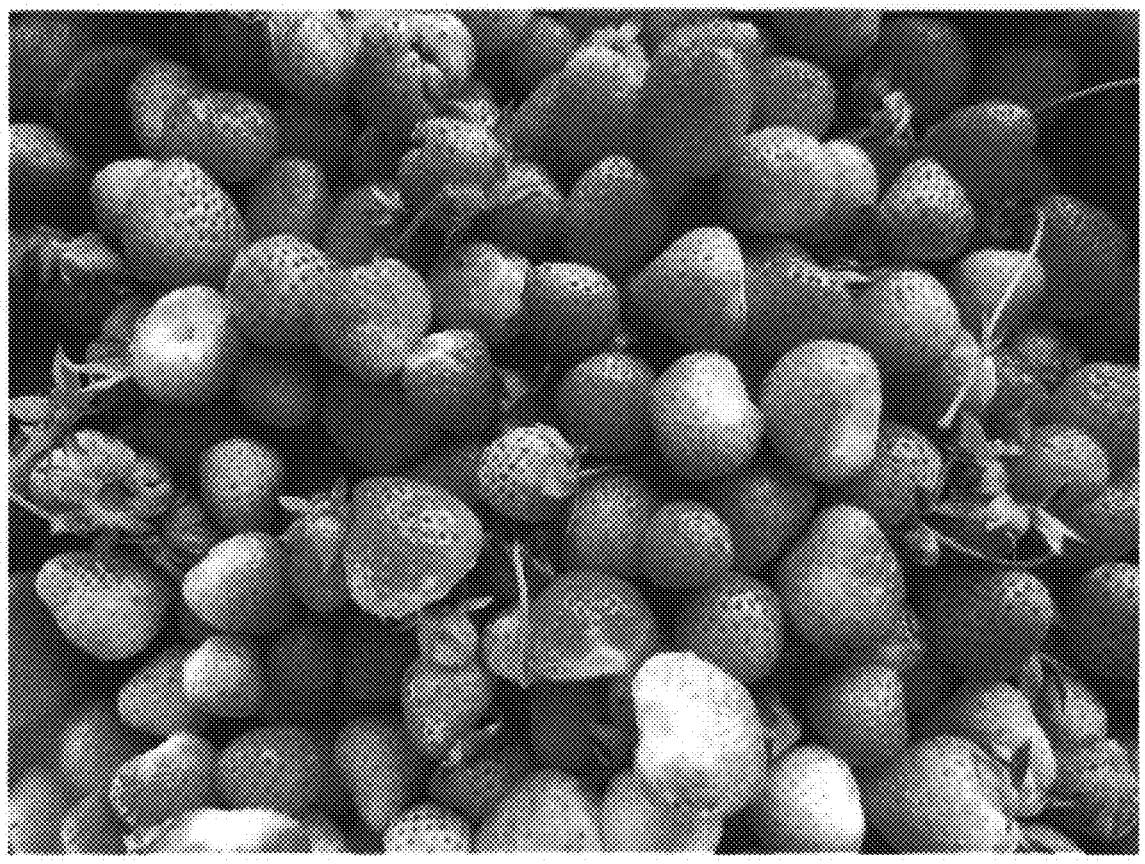
FIG. 9. A bowl of 'QBC-1' fruit showing the assortment of fruit shapes, uniformity and color during a normal early season harvest.

Fruit shape was spherical on smaller fruit and heart shaped or cordate with rounded shoulders on larger fruit (FIG. 9). Fruit is rarely misshapen, fasciated or eccentric to its main axis. Primary and secondary fruit had 18.2 seed per gram of flesh and fruit length was 2.8 cm wide and 2.9 cm long on average. Fruit flesh firmness is melting, giving a distinct buttery sensation. Fruit, either fresh or frozen, has a strong strawberry aroma, more intense than that of 'White Carolina' pineberry.

COMPARISON WITH PARENTAL AND COMMERCIAL VARIETIES

No cultivars have been found which contain the following species of *Fragaria* in combination: *Fragaria* x *ananassa* Duch., *Fragaria vesca* L., *Fragaria moschata* Duch. and *Fragaria nubicola* (Hook.f) Lindl. There are several cultivars of *Fragaria moschata* and *Fragaria vesca* and thousands of cultivars of *Fragaria* x *ananassa*, the hybrid species of *Fragaria chiloensis* (L.) Mill. and *Fragaria virginiana* Duch. commonly used in all commercial production.

Several cultivars of wild white fruited or light-colored strawberry fruit are known. Of note, 'Yellow Wonder' *Fragaria vesca* seed (unpatented), or plants grown from seed is available. The present strawberry variety 'QBC-1' is different from 'Yellow Wonder' in having different colored fruit which is larger, firmer and more flavorful.

'White Pine' ('White Carolina') strawberry (unpatented, US Department of Agriculture National Clonal Germplasm Repository number 555681), *Fragaria* x *ananassa*, has white fruit but does not produce red coloration on the "fruit flesh" (swollen receptacle) as does 'QBC-1'. Both cultivars produce red "seed" (achenes or the true fruit), especially on the sun exposed side of the fruit. 'QBC-1' is more productive than 'White Pine' and has more erect growth habit with greater fruit size and plant vigor.

A search of patented varieties which have similarities to the primary distinguishing factor of 'QBC-1', pink fruit and white flesh, revealed two other cultivars which have a similar fruit coloration. 'DrisStrawFiftySeven' (U.S. Plant Pat. No. 29,728) has skin noticeably darker, although the fruit flesh is similar in color. Achene (seed) coloration pattern is similar to 'QBC-1', occurring mostly on the sun lighted side of the fruit; however, 'DrisStrawFiftySeven' achenes have a more brownish tint (RHS 175A) compared to 'QBC-1' (RHS 46A). 'DrisStrawFiftySeven', like 'QBC-1', has a fruit cavity; however, no mention is made of the sepals remaining on the plant at picking, as occurs with 'QBC-1'. 'QBC-1', over the course of the harvest, has spherical small fruit with a length to width ratio almost equal producing conic primary fruit only under good growing conditions whereas 'DrisStrawFiftySeven' has greater than 2× larger fruit which is over twice as long as wide. 'QBC-1' fruit is noticeably softer than 'DrisStrawFiftySeven'.

'FL16.78-109' (U.S. Plant Pat. No. 33,477) fruit is described as white with a pink blush, considerably lighter than 'QBC-1'. 'FL16.78-109' fruit is firmer and over twice as large and heavy as 'QBC-1' and is conical and lacking a fruit cavity. Like 'QBC-1', 'FL16.78-109' is sweet tasting as is 'QBC-1', with 'QBC-1' having a higher peak fruit soluble solid concentration (brix).

'FL16.78-109' plants are moderately resistant to Powdery Mildew unlike the susceptibility of 'QBC-1'.

What is claimed is:

1. A new and distinct variety of strawberry plant named 'QBC-1' as illustrated and described herein.

* * * * *